United States Patent
Wolbring et al.

(10) Patent No.: US 7,951,120 B2
(45) Date of Patent: May 31, 2011

(54) METHOD FOR MANUFACTURING A SYRINGE

(75) Inventors: Peter Wolbring, St. Wendel (DE); Ralph Mosimann, Wuppenau (CH); Hanspeter Diem, Herisau (CH)

(73) Assignee: Schott AG, Mainz (DE)

( * ) Notice: Subject to any disclaimer, the term of this patent is extended or adjusted under 35 U.S.C. 154(b) by 2083 days.

(21) Appl. No.: 10/847,101

(22) Filed: May 17, 2004

(65) Prior Publication Data

US 2004/0254539 A1  Dec. 16, 2004

(30) Foreign Application Priority Data

Jun. 4, 2003  (DE) .................................. 103 26 706

(51) Int. Cl.
*A61M 5/315* (2006.01)
(52) U.S. Cl. ........................................ 604/220; 604/187
(58) Field of Classification Search .................. 604/218, 604/220–222, 227, 228, 187
See application file for complete search history.

(56) References Cited

U.S. PATENT DOCUMENTS

| | | | |
|---|---|---|---|
| 3,084,688 A * | 4/1963 | McConnaughey | ............ 604/232 |
| 5,250,030 A | 10/1993 | Corsich | |

FOREIGN PATENT DOCUMENTS

| | | |
|---|---|---|
| DE | 31 07 414 A1 | 9/1982 |
| DE | 43 18 142 C2 | 12/1994 |
| DE | 44 34 644 C2 | 4/1996 |
| DE | 199 29 325 A1 | 1/2001 |
| EP | 0 738 517 B1 | 10/1996 |
| EP | 0 764 450 A1 | 3/1997 |
| EP | 0 764 450 B1 | 3/1997 |
| EP | 0 864 372 B1 | 9/1998 |
| EP | 0 882 467 B1 | 12/1998 |
| EP | 0 980 276 B1 | 2/2000 |
| JP | 2001327600 A | 11/2001 |
| JP | 2003-199827 | 7/2003 |
| WO | 94/13339 | 6/1994 |
| WO | 94/26334 | 11/1994 |
| WO | 99/55402 | 11/1999 |
| WO | 00/07648 | 2/2000 |

* cited by examiner

*Primary Examiner* — Kevin C Sirmons
*Assistant Examiner* — Catherine N Witczak
(74) *Attorney, Agent, or Firm* — Harness, Dickey & Pierce, P.L.C.

(57) ABSTRACT

A syringe has a syringe barrel into which a plunger stopper is inserted during a manufacturing process. A plunger rod is connected to the plunger stopper, and a backstop for preventing inadvertent removal of the plunger stopper from the syringe barrel is arranged at the proximal end of the syringe barrel. The backstop and the plunger rod are configured to form a combined assembly component which is adapted to be mounted to the syringe barrel in a combined manufacturing step. After mounting the combined assembly component to the syringe barrel, the backstop and the plunger rod are separated to allow conventional use of the syringe.

28 Claims, 5 Drawing Sheets

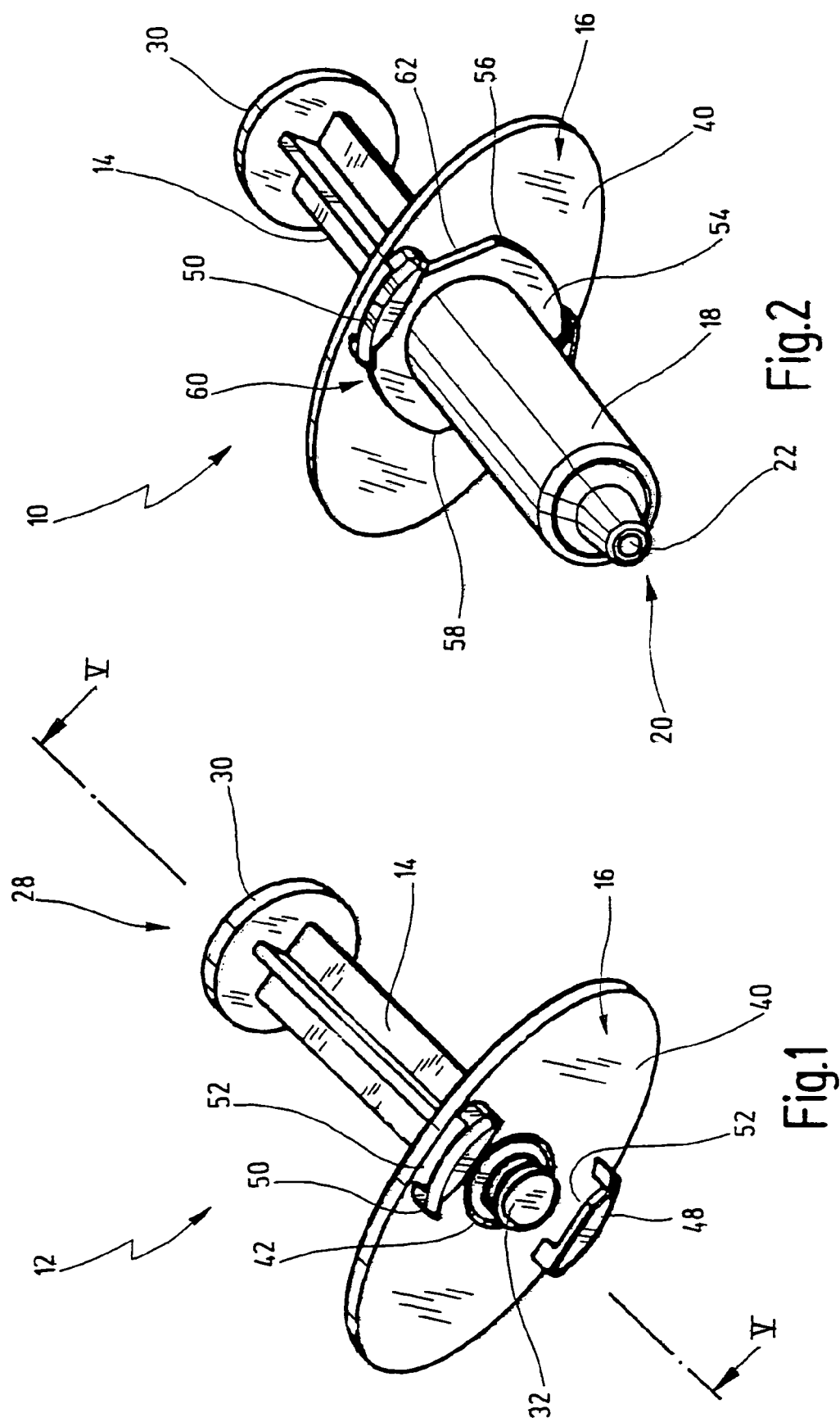

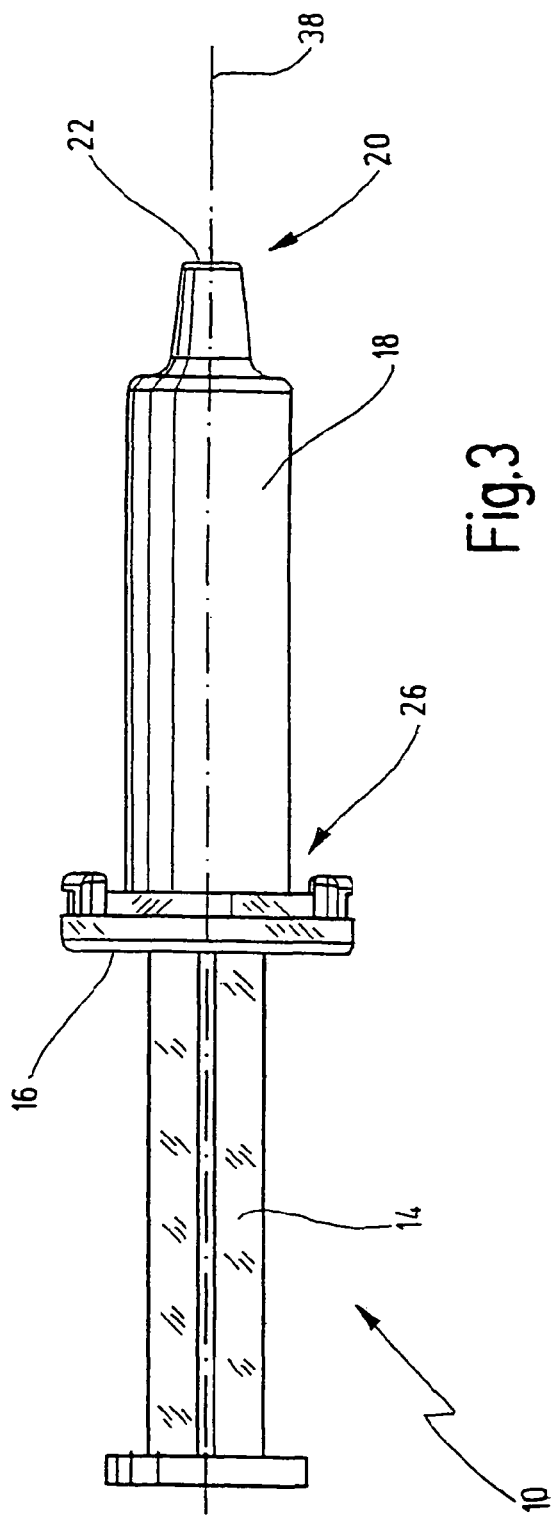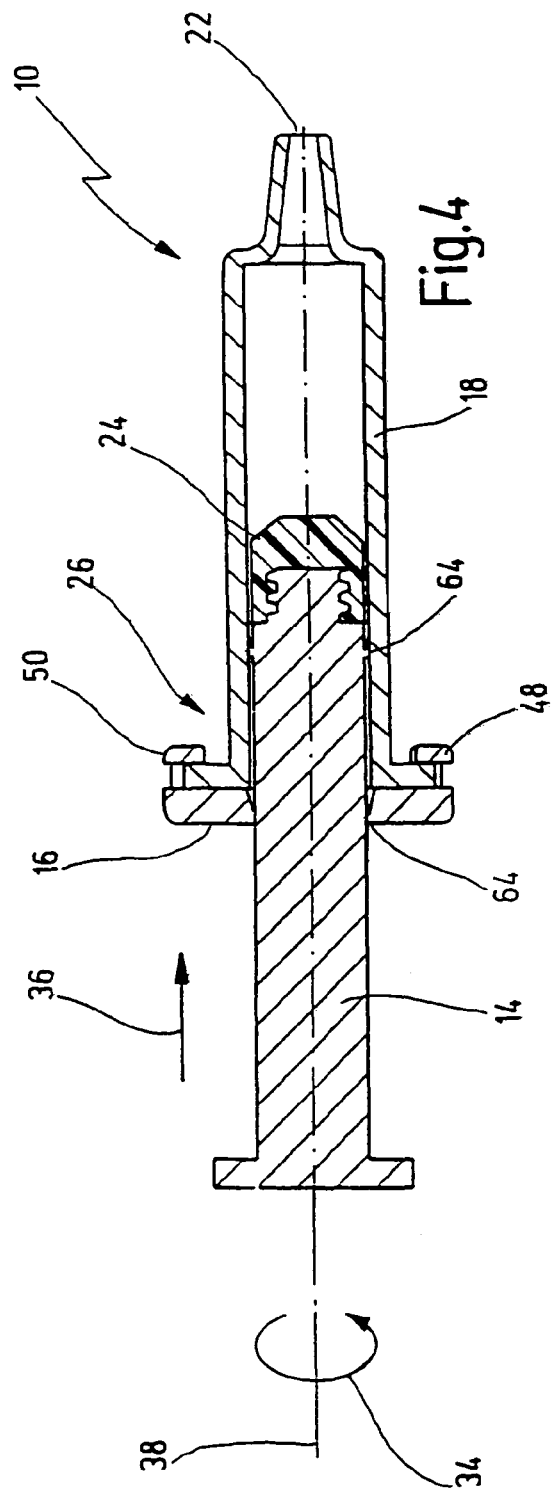

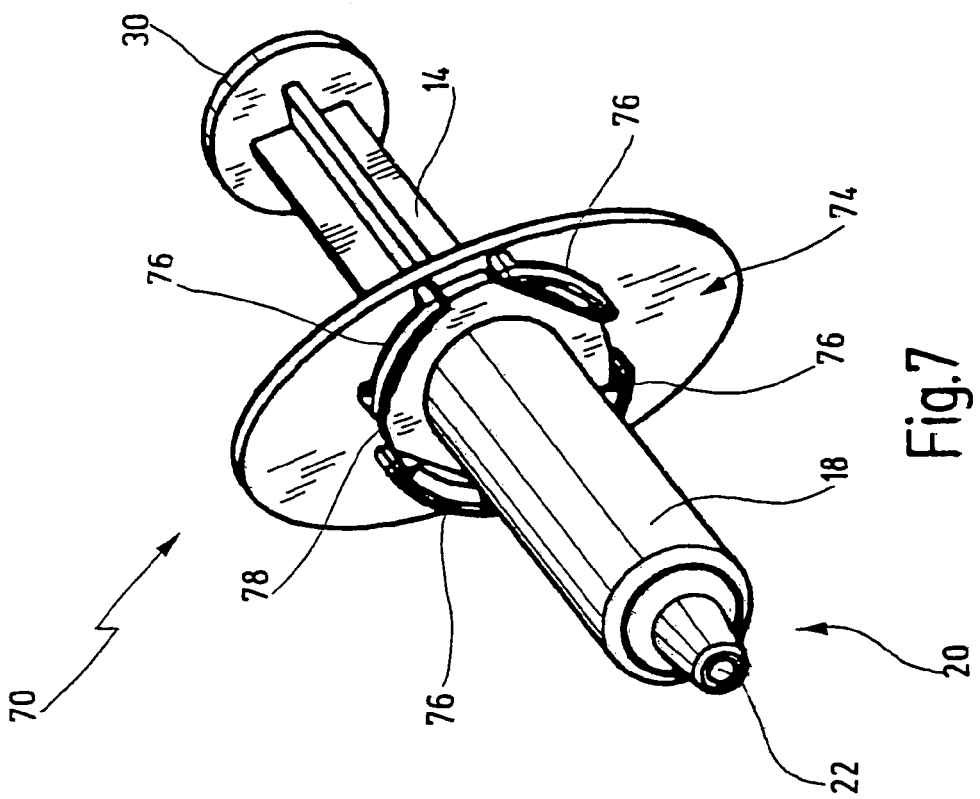
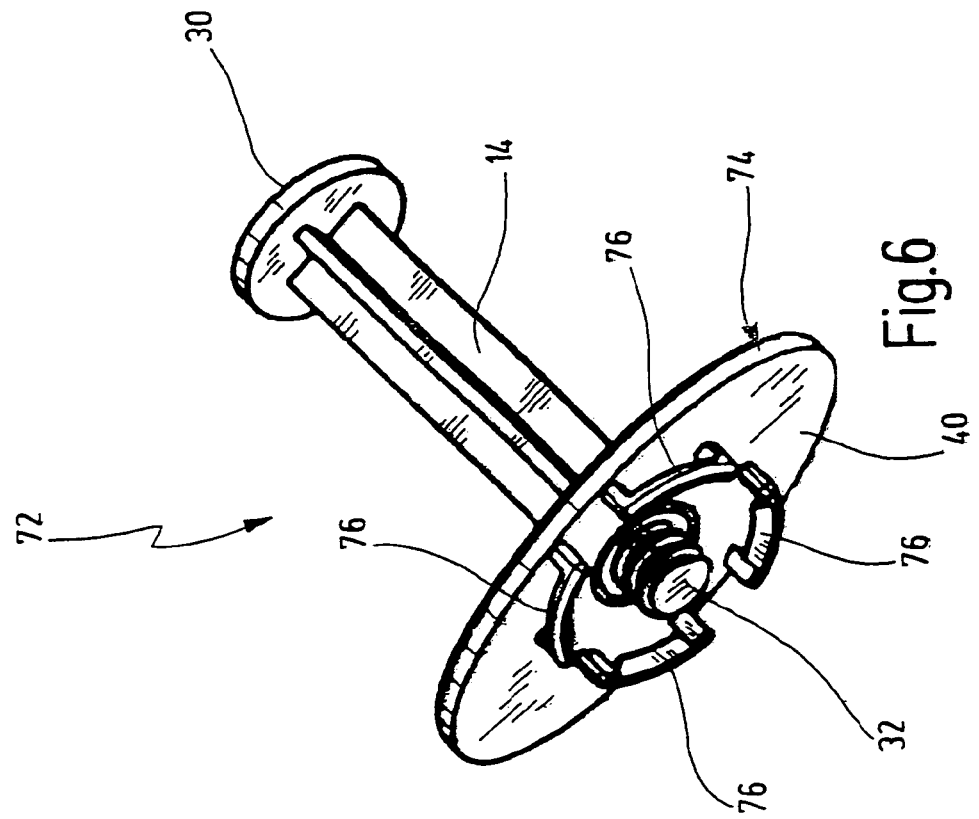

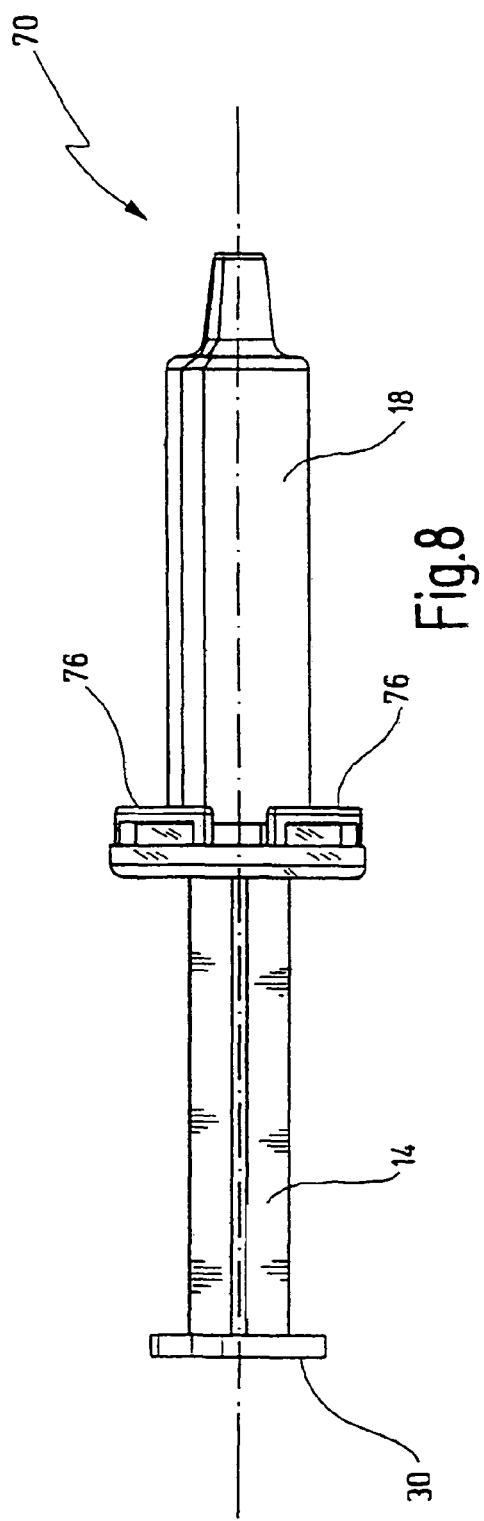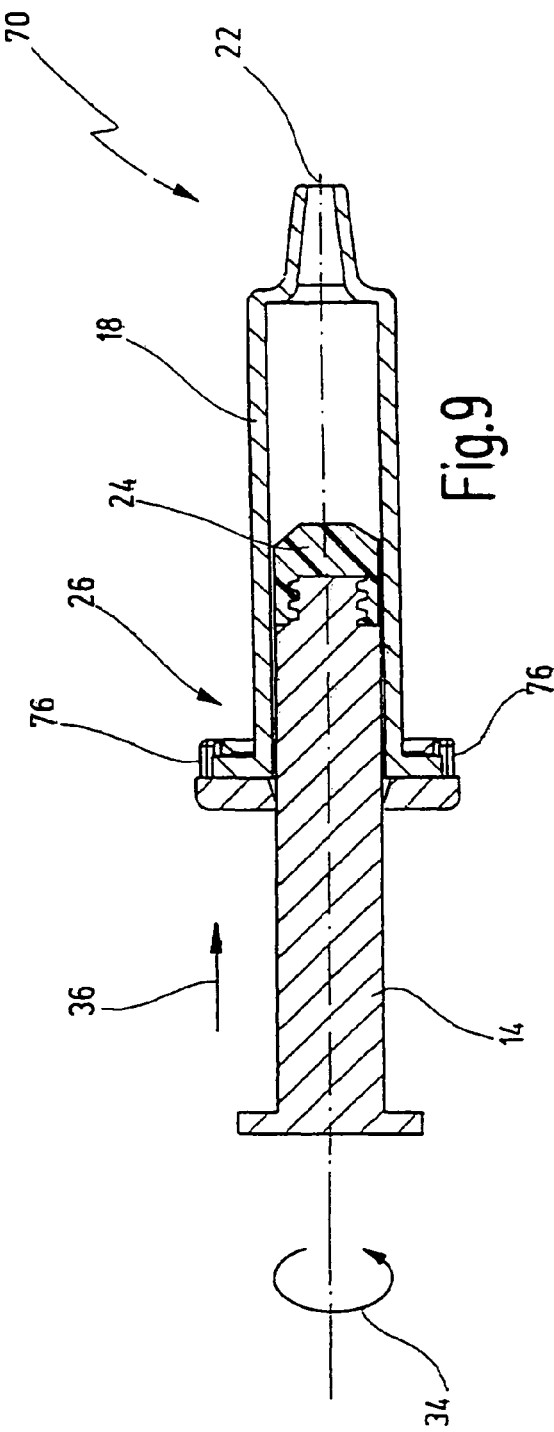

METHOD FOR MANUFACTURING A SYRINGE

The present invention relates to a method for manufacturing a syringe, in particular a syringe for medical applications, and further to a syringe manufactured in accordance with this method, and to a combined assembly component used in the manufacturing process according to the present invention. More specifically, the present invention relates to a syringe having a backstop arranged at the proximal end of a syringe barrel, and to a process of manufacturing the same.

BACKGROUND OF THE INVENTION

In the pharmaceutical industry, there are a number of medicaments which are already filled into medical syringes at the place of manufacture. The pharmaceutical manufacturer fills the medicament, under sterile conditions, into a sterile syringe barrel which is closed off at the distal end with a sealing cap. The syringe barrel is then closed off at the proximal end with a sterile plunger stopper, frequently made of rubber-elastic material. Thereafter, the plunger rod of the syringe is usually screwed into a suitably provided internal thread on the plunger stopper, the syringe is placed in a sterile package, and made ready for supply. A particular advantage of this procedure is that the medicament is in this way kept sterile until actual administration, which cannot always be guaranteed if, for example, the medicament is drawn into the syringe just before administration.

EP 0 764 450 B1 discloses a syringe which is well suited for application purposes of this kind because a backstop at the proximal end of the syringe barrel prevents the plunger stopper from being pulled out rearward, i.e. in the direction of the proximal end, after the syringe has been filled and assembled. Inadvertent removal of the plunger stopper, which would compromise sterility, can be ruled out in this way. In addition, a syringe having a backstop is particularly suitable for very expensive and/or highly toxic medicaments, for example anticancer agents, because, if the plunger stopper were inadvertently pulled out, the medicament contained in the syringe could escape and thus pose a hazard to the medical personnel or would at least represent an expensive loss.

A further preferred application of syringes with a backstop is when the medicament to be administered has to be prepared by being drawn up several times into the syringe. In these cases too, the backstop ensures that the plunger stopper cannot be inadvertently pulled back too far and thus removed from the syringe barrel.

In the syringe of EP 0 764 450 B1, the backstop consists of a grip plate and of a flange formed integrally thereon. After insertion of the plunger stopper into the syringe barrel, the backstop is fitted laterally onto the syringe barrel, i.e. orthogonally with respect to the longitudinal direction of the syringe and thus orthogonally with respect to the direction of movement of the plunger stopper. The finger plate and the flange have a lateral aperture permitting this lateral engagement or snap-fit onto the outer circumference of the syringe barrel. Moreover, the finger plate and the flange have, at the outer proximal end of the syringe barrel, an internal diameter which is smaller than the external diameter of the plunger stopper, by which means the backstop is formed.

WO 99/55402 discloses a syringe in which the backstop is formed by a projection arranged in the inside of the syringe barrel. Specially designed locking hooks are provided on the plunger rod of the syringe and these can snap over the projection in the direction of advance of the plunger rod, whereas they block it in the opposite direction.

WO 94/26334 discloses a prior art syringe in which the backstop is a flange which is fitted from the side at the proximal end of the syringe barrel. The flange has a bracket which protrudes into the inside of the syringe barrel and which prevents withdrawal of the plunger stopper.

In addition, there are a great many other alternatives in which a backstop is used to prevent inadvertent rearward withdrawal of the plunger stopper of a syringe. Reference is made, by way of example, to WO 94/13339, WO 00/07648, JP 2001-327600A, U.S. Pat. No. 5,250,030, DE 44 34 644 C2 or EP 0 738 517 B1. However, compared to syringes without a backstop, many of the known solutions require changes and/or additions to be made to the syringe barrel and/or to the plunger rod. This means that "conventional" syringes cannot be equipped with a corresponding backstop. As a result of this, these "special makes" are considerably more expensive than conventional syringes without a backstop.

The backstop known from aforementioned EP 0 764 450 B1 can, by contrast, be used on syringe barrels of standard design, in particular on ones with a circular flange. However, the backstop is fitted in a separate assembly step and, additionally, in a direction of movement which is transverse with respect to the direction of movement in which the plunger stopper is inserted into the syringe barrel. The additional assembly step, also deviating from the other movements, entails added costs going beyond the simple material costs for the backstop.

SUMMARY OF THE INVENTION

In vie of the above, it is an object of the present invention to provide a method for manufacturing a syringe with a backstop in a less complicated and less expensive manner.

It is another object of the present invention to provide a syringe having a backstop which is configured such that the syringe can be manufactured in a less complicated and less expensive manner.

It is yet another object of the present invention to provide an assembly component for manufacturing a syringe with a backstop in a less complicated and less expensive manner According to one aspect of the invention, these objects are achieved by a method comprising the steps of: a) providing a syringe barrel having a proximal end and a distal end, b) inserting a plunger stopper into the syringe barrel, c) mounting a plunger rod on the plunger stopper, and d) arranging a backstop at the proximal end of the syringe barrel, wherein the backstop is coupled with the plunger rod to form a combined assembly component prior to step c), and wherein steps c) and d) are executed as a combined manufacturing step using the combined assembly component.

According to another aspect, these objects are achieved by a method of manufacturing a syringe, the method comprising the steps of: a) providing a syringe barrel having a proximal end and a distal end, b) providing a combined assembly component, the combined assembly component comprising a backstop for the syringe and a plunger rod for the syringe which are separably coupled to each other, c) inserting a plunger stopper into the syringe barrel, and d) mounting the combined assembly component to the syringe barrel, wherein the backstop is arranged at the proximal end of the syringe barrel and the plunger rod is secured to the plunger stopper in a combined manufacturing step during step d).

According to yet another aspect of the invention, there is provided a syringe comprising a syringe barrel having a proximal end and a distal end, and comprising a plunger stopper, a plunger rod mounted to the plunger stopper, and a backstop preventing the plunger stopper from being removed from the syringe barrel, the backstop being arranged on the proximal end of the syringe barrel, wherein the backstop and the plunger rod are designed such that they can be coupled to each other to form a combined assembly component which is configured to be mounted to the syringe barrel in a combined manufacturing step.

According to yet another aspect of the invention, there is provided an assembly component for manufacturing a syringe, having a syringe barrel with a proximal end and a distal end, the assembly component comprising a plunger rod to be arranged in the syringe barrel and a backstop to be mounted at the proximal end of the syringe barrel, wherein the plunger rod and the backstop are coupled to each other such that they can be mounted to the syringe barrel in a combined manufacturing step.

The backstop and the plunger rod thus form, prior to final assembly of the plunger rod, a unit which is separated only later in the course of assembly. In this way, it is possible to guide the backstop onto the syringe barrel without any additional transport step, which reduces the number of assembly steps. In addition, no separate machine part is needed for guiding the backstop onto the syringe barrel, which likewise contributes to a cost reduction, because the novel syringes can in principle be assembled on the same machine as conventional syringes without backstop. A further advantage is that, as a result of the novel method, the backstop and the plunger rod can be produced in a common manufacturing process, which further reduces the number of necessary manufacturing steps.

The novel method and the further implementations of the invention are based inter alia on the idea of initially combining the backstop and the plunger rod and of separating them from one another only later, preferably during the course of assembly. However, it would also be possible to let the backstop and the plunger rod coupled until the syringe is used.

In preferred embodiments, which are explained in more detail below, it is intended that the backstop and the plunger rod are coupled materially, i.e. integrally, to form the combined assembly component. This means that separation involves a tearing off or breaking off of the material connection. Such a step is extremely unusual in the pharmaceutical industry, and in particular in the above-described filling of syringes under sterile conditions, since, upon breaking off/tearing off of a connection, very small particles are released which can lead to contamination of the medicament (or also of another substance which is to be produced and packaged under strict purity conditions). In the present case, however, use is made of the new realization that any particles which may possibly be present are unable to contaminate the sterile filled medicament because, at the time of separation of plunger rod and backstop, the syringe barrel is already closed by the plunger stopper. Contrary to all customary practices, it is therefore possible, in this particular case, to separate even a material connection without compromising the purity conditions critical for the pharmaceutical sector. However, instead of a material connection, it is also preferred to have a form-fit connection or force-fit connection of backstop and plunger rod, which allows to reassemble both parts, for example for multiple re-uses.

In a preferred embodiment of the invention, the backstop is guided onto the syringe barrel substantially parallel to a longitudinal axis thereof. The backstop is preferably connected concentrically to the plunger rod to form the combined assembly component.

Due to these embodiments, the number of necessary assembly steps and the number of necessary movements can be reduced still further. More particularly, the backstop and the plunger rod can be guided onto the syringe barrel in a single rectilinear movement which corresponds exactly to the movement customary in the manufacture of conventional syringes. In this embodiment, the novel method can therefore be integrated more easily into conventional manufacturing operations, which further reduces labor and costs.

In a further embodiment, the backstop is coupled with the plunger rod via predetermined break points in such a way that the backstop tears off from the plunger rod when said plunger rod is mounted on the plunger stopper.

Preferably, the backstop and the plunger rod each have tear-off points which together define at least one predetermined break point.

According to this preferred embodiment, the backstop and the plunger rod are coupled integrally to one another. This makes it possible to produce backstop and plunger rod in a single injection-molding process, which reduces costs very considerably. However, it is also possible to produce backstop and plunger rod in an at least two-step injection-molding process, this having the advantage that the backstop and the plunger rod can be made of different materials. As has already been mentioned further above, the tearing of the backstop from the plunger rod is not problematic in the present case, despite the sensitive field of application, because any microparticles arise outside the sterile area.

In a further preferred embodiment, the backstop is separated from the plunger rod with a rotational movement, and preferably with a rotational movement with which, in addition, the plunger rod is also screwed into the plunger stopper.

This embodiment leads to a further reduction of the assembly steps and movements because the separation of the backstop from the plunger rod is effected by the same movement which, in the prior art assembly operation, is provided as standard for securing (screwing) the plunger rod on the plunger stopper. In this embodiment, the novel method can be integrated into existing production operations more easily and at less cost.

In a further embodiment of the invention, the backstop is secured on the syringe barrel with a bayonet-like locking mechanism, said bayonet-like locking mechanism preferably having at least one holder into which there engages a projecting part of a flange arranged on the syringe barrel.

This embodiment is particularly advantageous for syringes in which the syringe barrel has what is called a DIN flange at the proximal end. The DIN flange, used widely in conventional syringes, is obtained as it were from a round flange, of which two opposite circle segments are separated at secants. The DIN flange is therefore not rotationally symmetrical, which thus makes securing with the aid of a bayonet-like locking mechanism particularly easy and efficient. In a preferred configuration, which is described in more detail below on the basis of an illustrative embodiment, two holders are arranged on the backstop, with each holder receiving one of the "corners" of the DIN flange in the course of the rotational movement. Tearing-off or separation of the backstop from the plunger rod is obtained particularly easily in this embodiment because the bayonet-like locking mechanism limits the angle of rotation of the backstop. Accordingly, the "normal" screwing of the plunger rod into the plunger stopper, which requires a much greater angle of rotation, inevitably produces a force which can advantageously be exploited for separating the backstop.

In a further embodiment, the plunger rod executes a translational movement when being mounted on the plunger stopper, the backstop being separated from the plunger rod with the translational movement.

A translational movement is also present as standard in conventional assembly operations because the plunger rod, when being screwed into the plunger stopper, also moves in the longitudinal direction of the syringe. This movement too can be used very effectively and thus inexpensively in order to separate the backstop, and, if appropriate, also in combination with the rotational movement already explained further above. In suitable cases, however, the translational movement of the plunger rod can also be used on its own for separating the backstop, for example if the plunger rod, deviating from the course described above, is not screwed into the plunger stopper but is connected in some other way to the plunger stopper.

In a further embodiment, the backstop is arranged on the syringe barrel with snap-fit elements which engage around a flange arranged on the syringe barrel. The snap-fit elements are preferably in the form of a segmental ring which engages around a circular flange arranged at the proximal end of the syringe barrel and tears off upon advance of the plunger rod (translational movement).

This embodiment is particularly advantageous if the syringe barrel has a rotationally symmetrical design at its proximal end, because in this case a bayonet-like locking mechanism would constitute an additional expense. Therefore, this embodiment is particularly cost-effective and efficient for syringe barrels with a circular flange.

In a further embodiment, the backstop has at least one side area protruding like a wing and forming an ergonomic finger support. In a presently preferred illustrative embodiment, the backstop has, for example, an elliptical collar which forms two such wings.

It will be appreciated that the features mentioned above and the features still to be explained below can be used not only in the respectively cited combination, but also in other combinations or in isolation, without departing from the scope of the present invention.

BRIEF DESCRIPTION OF THE DRAWINGS

Illustrative embodiments of the invention are explained in more detail in the following description and are shown in the drawing, in which:

FIG. 1 shows a plunger rod and a backstop as a combined assembly component according to a first illustrative embodiment, FIG. 2 shows a syringe using the assembly component from FIG. 1, FIG. 3 shows the syringe from FIG. 2 in a side view, FIG. 4 shows the syringe from FIG. 3 in a cross-sectional view, the plunger rod in this case having already been pushed further into the syringe barrel, FIG. 6 shows an assembly component consisting of backstop and plunger rod according to a further illustrative embodiment, FIG. 7 shows a syringe with the assembly component from FIG. 6, FIG. 8 shows the syringe from FIG. 7 in a side view, and FIG. 9 shows the syringe from FIG. 8 in a cross-sectional view, the plunger rod having already been pushed into the syringe barrel.

DESCRIPTION OF PREFERRED EMBODIMENTS

Figure 5:
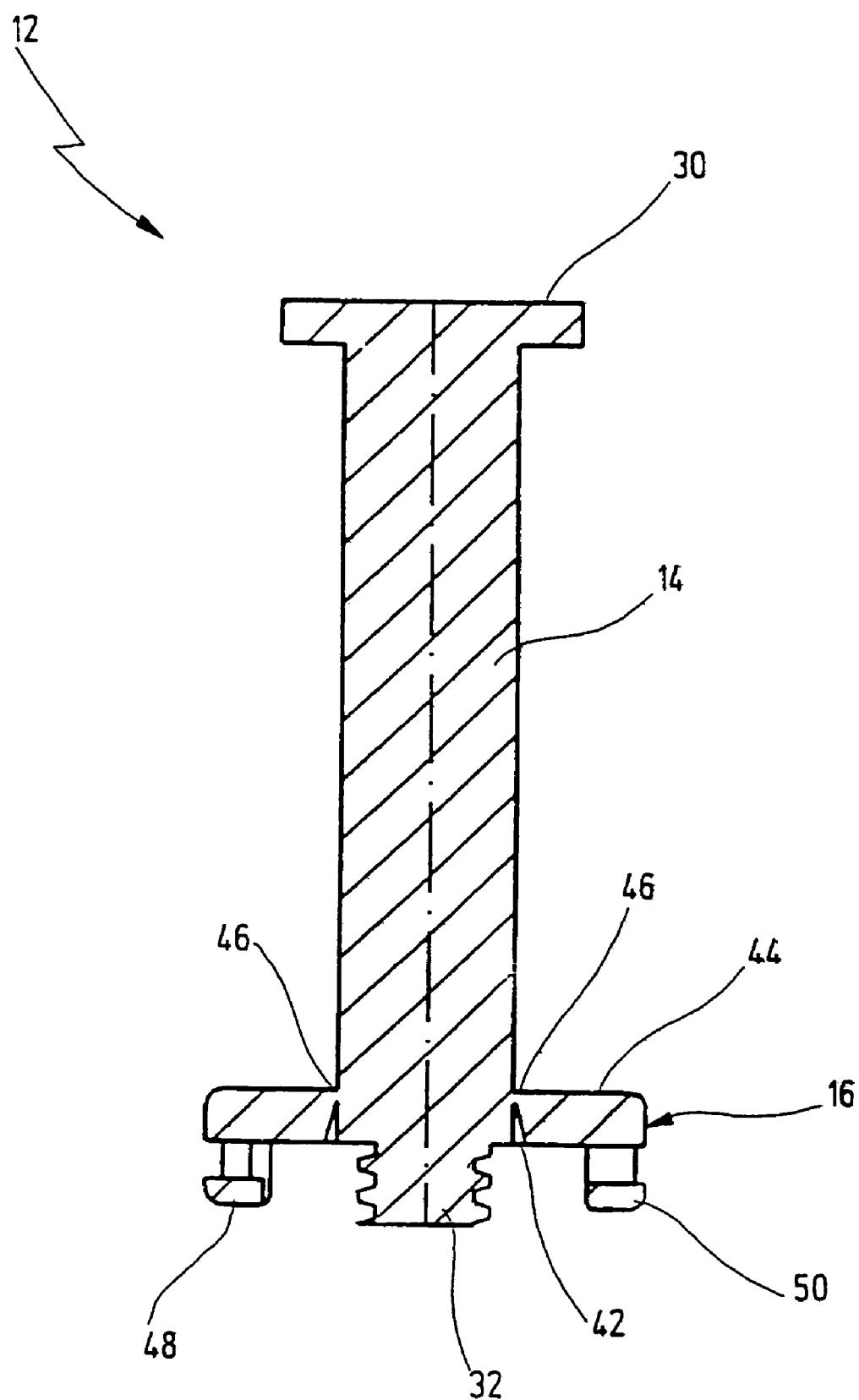
FIG. 5 shows the assembly component from FIG. 1 in an enlarged cross-sectional view along the line V-V in FIG. 1.

In FIGS. 1 to 4, a syringe manufactured in accordance with the novel method is designated in its entirety by reference number 10.

The syringe 10 is manufactured using an assembly component 12 which includes the subsequent plunger rod 14 and the subsequent backstop 16. Before final assembly of the syringe 12, plunger rod 14 and backstop 16 are materially connected to form the assembly component shown in FIG. 1.

Reference number 18 designates a syringe barrel which, in a manner known per se, has an opening 22 at its distal end 20. A cannula can be secured to the opening 22. Before its final assembly, the syringe 10 is preferably filled with a medicament (not shown here) and then closed with a plunger stopper 24 (FIG. 4) at the proximal end 26. This is usually done under sterile conditions by the pharmaceutical manufacturer of the medicament. For the sake of completeness, it should however be noted that the present invention is not limited solely to syringes for these application purposes, and instead it can also be used in all other medical syringes and, in addition, also in syringes for the non-medical sector.

At its proximal end 28, the plunger rod 14 has an end plate 30 which, during use of the syringe, serves as a support surface, for example for the physician's thumb. The support plate 30 is adjoined by the actual plunger rod which, at its front end, runs out in a threaded stub 32. In the area between end plate 30 and threaded stub 32, the plunger rod 14 here has a profile of cross-shaped section, as is known from syringes of the generic type. However, the invention is not limited to this, i.e. the plunger rod can also have any other desired profile.

As is shown in FIG. 4, upon final assembly of the syringe 10, the plunger rod 14 is screwed into the plunger stopper 24 which has already been inserted into the syringe barrel 18. The rotational movement required for this is indicated by an arrow 34 in FIG. 4. In addition, when being secured on the plunger stopper 24, the plunger rod 14 also executes a translational movement in the direction of an arrow 36. This translational movement extends parallel to and along the longitudinal axis 38 of the syringe 10. The insertion of the plunger rod 14 into the syringe barrel 18 is to this extent known to the skilled persons in this field.

In the illustrative embodiment shown here, the backstop 16 has an elliptical plate 40 which extends transversely with respect to the longitudinal axis 38 of the syringe 10 and thus also transversely with respect to the plunger rod 14. With the syringe 10 assembled, the plate 40 serves as a finger support, and it facilitates the maneuvering of the syringe 10.

Provided at the center of plate 40 there is an annular groove 42 which concentrically surrounds the threaded stub 32 of the plunger rod 14. As is illustrated in FIG. 5, the groove 42 in the assembly component 12, i.e. before final assembly of the syringe 10, is not formed all the way to the bottom 44 of the plate 40. Instead, the groove 42 has the function of a material weakening, which represents a predetermined break point between the plunger rod 14 and the backstop 16. As will be explained in more detail below, upon final assembly of the syringe 10, the plunger rod 14 and the backstop 16 are separated from one another at this predetermined break point and from then on constitute two separate component parts of the syringe 10.

In a preferred illustrative embodiment, the groove 42, along its circumference, is formed in some areas as far as the bottom 44 of the plate 40 (not discernible in the cross-sectional view in FIG. 5), so that the plunger rod 14 and the backstop 16 are connected to one another only as it were by small bridges 46 along the groove 42. This configuration affords a particularly simple and effective separation of the plunger rod 14 from the backstop 16 when screwing the plunger rod 14 into the plunger stopper 24.

In the illustrative embodiment preferred here, two holders 48, 50 are arranged on that side of the plate 40 pointing to the distal end 20 of the syringe barrel 18. The two holders 48, 50 each consist of a U-shaped part which is connected with its two free branches integrally to the plate 40. The two holders 48, 50 thus each form an insert opening 52 by means of which the backstop 16 can be secured on the proximal end 26 of the syringe barrel 18. In the illustrative embodiment preferred here, the two holders 48, 50 are arranged with point symmetry in relation to the free end of the threaded stub 32.

The assembly component 12 formed in this way is preferably provided for securing to syringe barrels 18 with what is called a DIN flange. Such a DIN flange is designated in FIG. 2 by reference number 54. A characteristic of the DIN flange is the four corners, of which two are indicated in FIG. 2 by reference numbers 56 and 58. In the view in FIG. 2, two further corners, which lie symmetrically with respect to the corners 56, 58, engage in the insert openings 52 of the two holders 48, 50 and thus fix the backstop 16 on the syringe barrel 18. Since the DIN flange 54 is not rotationally symmetrical, because of the corners 56, 58, this design provides a bayonet-like locking mechanism between the backstop 16 and the syringe barrel 18. This kind of locking mechanism is designated as a whole here by reference number 60. For locking or securing, the plate 40 of the backstop 16 is fitted onto the DIN flange 54 in such a way that the rectilinear sides 62 of the DIN flange 54 come to lie parallel with the two holders 48, 50. By means of the rotational movement 34, which at the same time serves to screw the plunger rod 14 into the plunger stopper 24, the corners of the DIN flange 54 which are not discernible in FIG. 2 turn into the insert openings 52 and lock the plate 40 on the DIN flange 54. Since this locking procedure is completed after just a small angle of rotation, but the plunger rod 14 is turned further in the direction of the arrow 34 for screwing it into the plunger stopper 24, the plate 40 and thus the backstop 16 tear away from the plunger rod 14 at the predetermined break points 46. The backstop 16 is thus secured in the same operating step and with the aid of the same movement with which the plunger rod 14 is also mounted on the syringe barrel 18 and the plunger stopper 24.

The view in FIG. 4 shows a situation after the backstop 16 has been secured on the flange 54 of the syringe barrel 18 and after the plunger rod 14 has been torn from the plate 40 of the backstop 16. Remaining tear-off points are designated by reference number 64 in FIG. 4.

In the following description of a further preferred illustrative embodiment, identical reference numbers designate the same elements as before.

In FIGS. 6 to 9, a second illustrative embodiment of the novel syringe is designated in its entirety by reference number 70. The syringe 70 is manufactured using an assembly component 72 which differs from the assembly component 12 from FIG. 1 in terms of the way in which it is secured on the syringe barrel 18. More particularly, the backstop designated here by reference number 74 has, on its underside pointing to the distal end 22 of the syringe barrel 18, four holders 76 which are arranged in the manner of a segmental ring around the threaded stub 32 of the plunger rod 14. The holders 76 form snap-fit or locking means which, when the backstop 74 is pushed onto the syringe barrel 18 in the direction of the arrow 36, engage over the flange 78 of the syringe barrel 18. In this illustrative embodiment, the flange 78 can be a DIN flange as in the preceding illustrative embodiment, but it can also be a round flange or any other flange shape. To permit the snap-fit, the holders 76 in the present illustrative embodiment are made thinner and thus more flexible than the holders 48, 50 in the illustrative embodiment according to FIG. 1. Otherwise, however, the backstop 74 corresponds to the backstop 16 already described.

In these illustrative embodiments, the syringe barrel 18, backstop 16, 74 and plunger rod 14 are made of a polymer substance. This means that the backstop 16, 74 and the plunger rod 14 can be produced in a one-step injection-molding process. As an alternative to this, it is also possible to form the backstop 16, 74 on the plunger rod 14 in a two-step injection-molding process, so that different materials can be used. In general, however, materials other than polymer substances can also be used; for example, the syringe barrel 18 could be made of glass.

In the preferred illustrative embodiments shown here, the plunger rod 14 and the backstop 16, 74 are materially connected to form the combined assembly component 12, 72. It will be appreciated that, in further modifications, another connection of backstop and plunger rod is generally likewise possible, for example a force-fit connection and/or a form-fit connection. For example, the backstop 16, 74 can have a bore through which the threaded stub 32 of the plunger rod 14 passes, the internal diameter of the bore being chosen so that the plunger rod can slide through the bore only when a predetermined force is applied. Furthermore, the rotational movement 34 provided for screwing the plunger rod 14 in can be used to release the backstop 16, 74 from a form-fit connection with the plunger rod 14.

In all these cases, the backstop 16, 74 does not necessarily prevent the plunger rod 14 from being drawn back out of the syringe barrel 18. However, by suitable adaptation of the geometries, which is something familiar to the skilled person in this field, the backstop 16, 74 can be so designed that withdrawal of the plunger stopper 24 in the direction of the proximal end 26 of the syringe barrel 18 is impossible. In the simplest case, the internal diameter of the through-opening provided for the plunger rod 14 in the backstop 16, 74 only needs to be smaller than the external diameter of the plunger stopper 24.

What is claimed is:

1. A method for manufacturing a syringe, the method comprising the steps of:
    a) providing a syringe barrel having a proximal end and a distal end,
    b) inserting a plunger stopper into the syringe barrel,
    c) mounting a plunger rod on the plunger stopper, and
    d) arranging a backstop at the proximal end of the syringe barrel,
    wherein the backstop is coupled with the plunger rod to form a combined assembly component prior to step c),
    wherein steps c) and d) are executed as a combined manufacturing step using the combined assembly component; and further
    wherein the combined assembly component comprises predetermined break points which are configured such that the backstop tears off from the plunger rod when the plunger rod is mounted on the plunger stopper.

2. The method of claim 1, wherein the plunger rod and the backstop are automatically separated during the combined manufacturing step.

3. The method of claim 1, wherein the syringe barrel defines a longitudinal axis, the backstop being guided onto the syringe barrel substantially parallel to the longitudinal axis during the combined manufacturing step.

4. The method of claim 1, wherein the backstop is coupled concentrically to the plunger rod to form the combined assembly component.

5. The method of claim 1, wherein the backstop and the plunger rod are integrally formed to provide the combined assembly component.

6. The method of claim 5, wherein the backstop and the plunger rod are formed by an injection-molding process.

7. The method of claim 6, wherein the injection-molding process is at least a two-step injection-molding process forming the plunger rod and the backstop in a separated injection-molding steps.

8. The method of claim 1, wherein the backstop is separated from the plunger rod by means of a rotational movement.

9. The method of claim 8, wherein the rotational movement is additionally used to screw the plunger into the plunger stopper.

10. The method of claim 8, wherein the backstop is arranged on the syringe barrel by means of a bayonet-like locking mechanism.

11. The method of claim 10, wherein the bayonet-like locking mechanism comprises at least one holder arranged on the backstop and a projecting part arranged on the syringe barrel, the projecting part engaging into the holder during the combined manufacturing step.

12. The method of claim 11, wherein the syringe barrel comprises a flange at the proximal end, the flange forming the projecting part.

13. The method of claim 1, wherein the backstop is separated from the plunger rod during a translational movement of the plunger rod.

14. The method of claim 13, wherein the plunger rod executes the translational movement when being mounted on the plunger stopper, the backstop being separated from the plunger rod as a consequence of the translational movement.

15. The method of claim 13, wherein the backstop comprises at least one snap-fit element and the syringe barrel comprises a flange, the at least one snap-fit element engaging around the flange for securing the backstop at the proximal end of the syringe barrel during the combined manufacturing step.

16. The method of claim 1, wherein the syringe barrel is filled with a medicament prior to inserting the plunger stopper.

17. A method of manufacturing a syringe, the method comprising the steps of:
 a) providing a syringe barrel having a proximal end and a distal end,
 b) providing a combined assembly component, the combined assembly component comprising a backstop for the syringe and a plunger rod for the syringe which are separably coupled to each other,
 c) inserting a plunger stopper into the syringe barrel, and
 d) mounting the combined assembly component to the syringe barrel,
 wherein the backstop is arranged at the proximal end of the syringe barrel and the plunger rod is secured to the plunger stopper in a combined manufacturing step during step d), and further
 wherein the plunger rod and the backstop are automatically separated during the combined manufacturing step.

18. A syringe comprising a syringe barrel having a proximal end and a distal end, and comprising a plunger stopper arranged in a syringe barrel, a plunger rod mounted to the plunger stopper, and a backstop preventing the plunger stopper from being removed from the syringe barrel, the backstop being arranged on the proximal end of the syringe barrel, wherein the backstop and the plunger rod are designed such that they can be coupled to each other to form a combined assembly component which is configured to be mounted to the syringe barrel in a combined manufacturing step, and further wherein the backstop and the plunger rod each have tear-off points which together define at least one predetermined break point.

19. The syringe of claim 18, wherein the backstop and the plunger rod are configured to become separated during the course of mounting to the syringe barrel.

20. An assembly component for manufacturing a syringe having a syringe barrel with a proximal end and a distal end, the assembly component comprising a plunger rod to be arranged in the syringe barrel and a backstop to be mounted at the proximal end of the syringe barrel, wherein the plunger rod and the backstop are coupled to each other such that they can be mounted to the syringe barrel in a combined manufacturing step, and further comprising at least one predetermined break point where the backstop and the plunger rod can be separated from each other.

21. The assembly component of claim 20, wherein the plunger rod defines a longitudinal axis, the assembly adapted to being guided onto the syringe barrel substantially parallel to the longitudinal axis during the combined manufacturing step.

22. The assembly component of claim 20, wherein the backstop is coupled concentrically to the plunger rod.

23. The assembly component of claim 20, wherein the backstop is adapted to be separated from the plunger rod by means of a rotational movement.

24. The assembly component of claim 20, further comprising at least one holder arranged on the backstop, the holder being part of a bayonet-like locking mechanism for mounting the backstop to the proximal end of syringe barrel.

25. The assembly component of claim 20, wherein the backstop is adapted to be separated from the plunger rod by means of a translational movement.

26. The assembly component of claim 25, wherein the backstop comprises at least one snap-fit element adapted to be attached to the proximal end of the syringe barrel.

27. An assembly component for manufacturing a syringe having a syringe barrel with a proximal end and a distal end, the assembly component comprising a plunger rod to be arranged in the syringe barrel and a backstop to be mounted at the proximal end of the syringe barrel, wherein the plunger rod and the backstop are coupled to each other such that they can be mounted to the syringe barrel in a combined manufacturing step and further wherein the backstop and the plunger rod are integrally formed by an injection-molding process.

28. The assembly component of claim 27, wherein the backstop and the plunger rod are made from different materials in an at least two-step injection-molding process.

* * * * *